United States Patent [19]
Gabbay

[11] Patent Number: 6,090,140
[45] Date of Patent: Jul. 18, 2000

[54] EXTRA-ANATOMIC HEART VALVE APPARATUS

[75] Inventor: Shlomo Gabbay, Short Hills, N.J.

[73] Assignee: Shelhigh, Inc., Millburn, N.J.

[21] Appl. No.: 09/251,968

[22] Filed: Feb. 17, 1999

[51] Int. Cl.$^7$ .................................................. A61F 2/24
[52] U.S. Cl. ........................................ 623/2.1; 623/2.11
[58] Field of Search ........................... 623/2.1, 2.12, 623/2.2, 3.1, 3.26, 3.3

[56] References Cited

U.S. PATENT DOCUMENTS

| | | | |
|---|---|---|---|
| 4,195,623 | 4/1980 | Zeff | 623/3.1 |
| 5,178,634 | 1/1993 | Martinez | 623/2.1 |
| 5,332,403 | 7/1994 | Kolff | 623/3.26 |
| 5,509,930 | 4/1996 | Love | 623/2.1 |
| 5,545,215 | 8/1996 | Duran | 623/2.1 |

*Primary Examiner*—Michael J. Milano
*Attorney, Agent, or Firm*—Amin, Eschweiler & Turocy, LLP

[57] ABSTRACT

An extra-anatomic heart valve apparatus, which may be mounted externally to the heart, includes a heart valve positioned within a generally tubular conduit. An elongated outflow conduit extends from the tubular conduit and terminates in an end spaced from the heart valve. A resilient support and/or corrugations may be added to the outflow conduit to help resist compression of the conduit as well as to facilitate bending thereof.

29 Claims, 4 Drawing Sheets

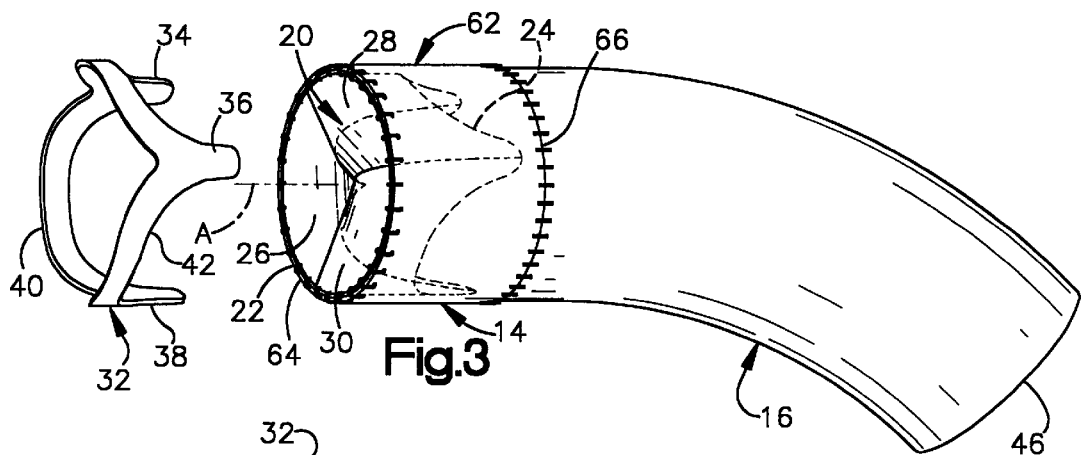
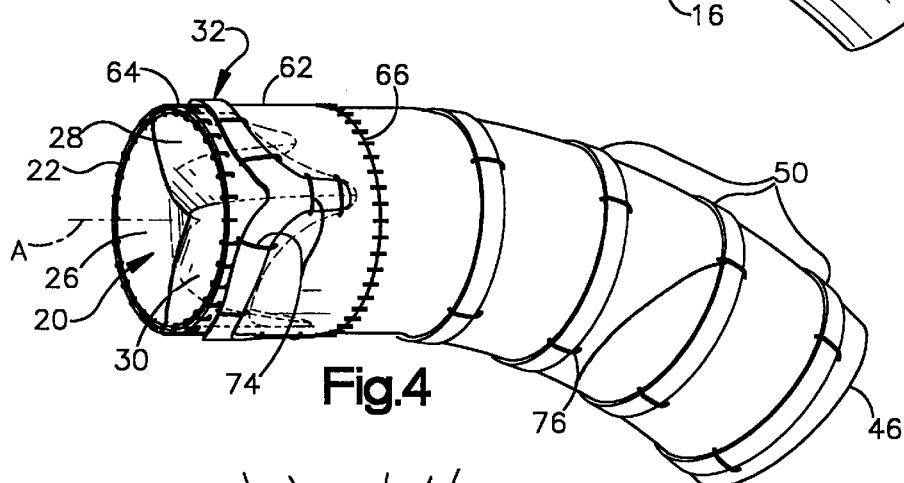
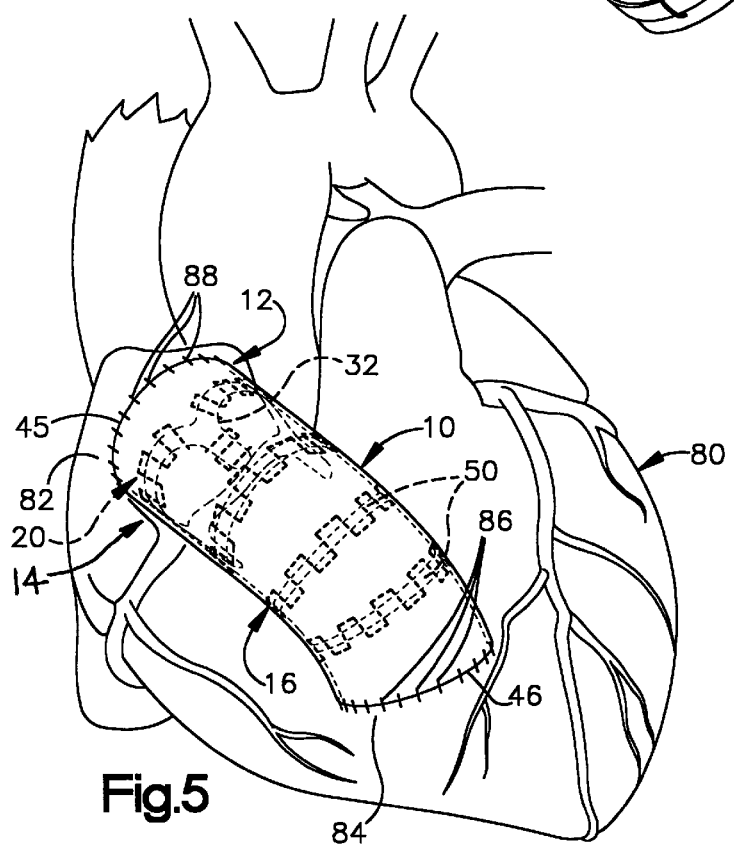

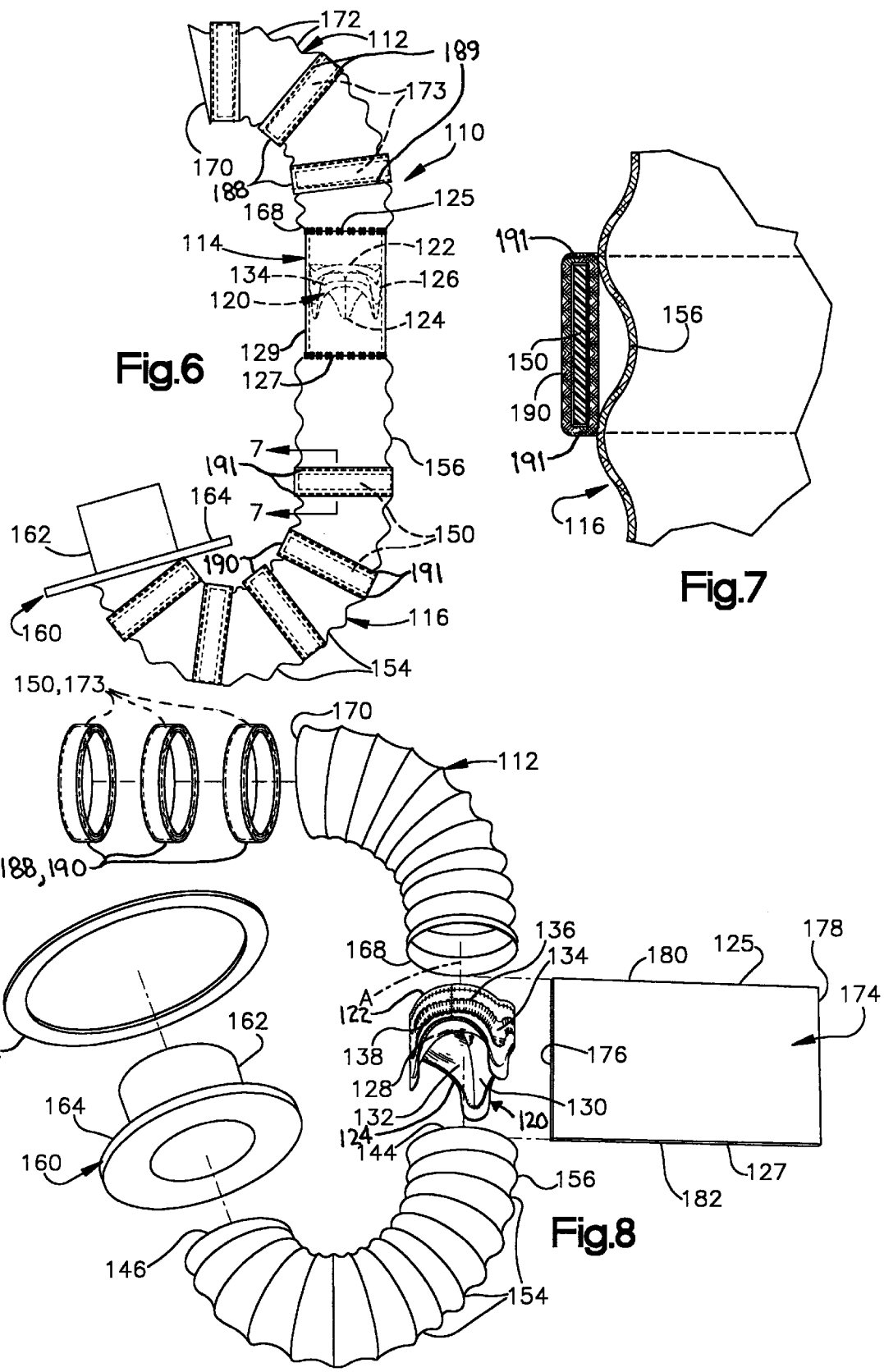

EXTRA-ANATOMIC HEART VALVE APPARATUS

TECHNICAL FIELD

The present invention relates generally to a heart valve apparatus and, more particularly, to an extra-anatomic heart valve apparatus.

BACKGROUND OF THE INVENTION

When an atrio-ventricular cardiac valve, such as a tricuspid or mitral valve, is diseased, it may be replaced by heart valve prosthesis. Such heart valve prostheses may include mechanical heart valves, natural tissue heart valves, or combinations thereof. A surgical procedure for replacing such a valve poses a serious risk and usually requires placing the patient on cardiopulmonary bypass during the procedure. With a patient on cardiopulmonary bypass, the surgical procedure is not only more difficult, but also poses a greater risk of morbidity and mortality to the patient. Such risks increase when a patient has been diagnosed with mitral or pulmonic valve stenosis or insufficiency.

SUMMARY OF THE INVENTION

The present invention is directed to an extra-anatomic anatomic heart valve apparatus that includes a heart valve having an inflow end, an outflow end, and a central axis extending through the inflow and outflow ends. An elongated outflow conduit extends longitudinally from the outflow end of the heart valve and terminates in a distal end spaced from the heart valve.

In one embodiment, at least one resilient support is disposed about the outflow conduit to help resist compression of the conduit. The support also is covered with a biological material to promote biocompatibility.

In another embodiment, the outflow conduit may include a plurality of corrugations formed in the sidewall of the outflow conduit to facilitate bending thereof.

BRIEF DESCRIPTION OF THE DRAWINGS

Preferred embodiments of the present invention are illustrated in the accompanying drawings in which:

FIGS. 2–4 illustrate fabrication steps for the heart valve of FIG. 1;

FIG. 5 illustrates the heart valve apparatus of FIG. 1 mounted to a heart in accordance with a preferred embodiment of the present invention;

FIG. 6 is a heart valve apparatus in accordance with a second embodiment of the present invention;

FIG. 7 is a partial sectional view of the apparatus of FIG. 6;

FIGS. 8 is an exploded view of the apparatus of FIG. 6;

DESCRIPTION OF PREFERRED EMBODIMENTS

Figure 1:
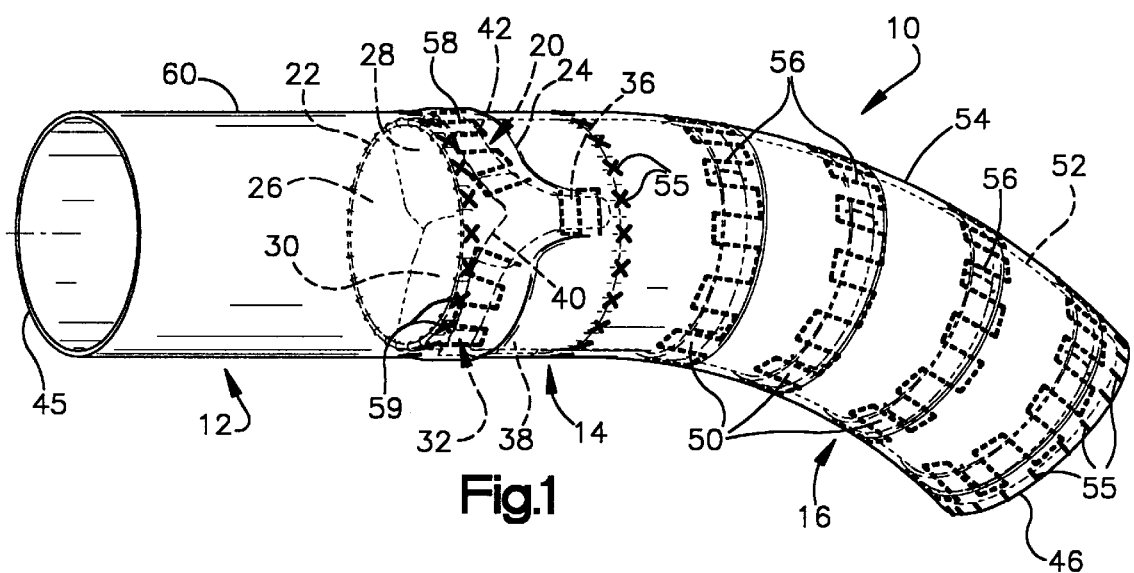
FIG. 1 is a heart valve apparatus in accordance with a first embodiment of the present invention.

FIG. 1 illustrates a first embodiment of an extra-anatomic anatomic heart valve apparatus 10 in accordance with the present invention. The apparatus 10 is defined by three substantially tubular portions, namely an inflow conduit 12, an intermediate heart valve conduit portion 14 and an elongated outflow conduit 16. Each of these portions 12, 14 and 16 may be formed of separate generally cylindrical conduits or, alternatively, some of the conduit portions may be part of the same elongated conduit. The inflow and outflow conduit portions 12 and 16 are in fluid contact with intermediate conduit portion 14.

The intermediate conduit 14 includes a heart valve 20 having an inflow end 22 and an outflow end 24. The heart valve 20 preferably has three leaflets 26, 28 and 30 which are movable to open and close in response to the flow of blood therethrough. Preferably, a substantially flexible stent element 32 is disposed about the heart valve 20 intermediate the inflow and outflow ends 22 and 24, respectively, to provide additional structural rigidity to inhibit stenosis of the valve. The inflow and outflow ends 22 and 24 of the heart valve 20 are defined by the attachment of valve leaflets 26, 28 and 30 along the generally cylindrical valve wall that surrounds the leaflets. Referring to FIGS. 1 and 3, the stent element 32 preferably includes stent posts 34, 36 and 38 which are positioned as to extend axially along the outer valve wall at the juncture of adjacent valve leaflets 26, 28 and 30. The stent element 32 also has inflow and outflow ends 40 and 42, preferably contoured according to the respective inflow and outflow ends 22 and 24 of the heart valve 20. The inflow and outflow ends 40 and 42 of the stent element 32 are spaced from the respective inflow and outflow ends 22 and 24 of the heart valve 20 so that the stent element is positioned substantially midway between the inflow and outflow ends of the valve. Preferred embodiments of suitable stent elements are disclosed in copending U.S. application Ser. No. 052,707 and U.S. Pat. No. 5,855,602 and U.S. Pat. No. 5,861,028. Of course, other stents and stentlike structures also may be used to support the heart valve 20. Such stent elements may be formed of resilient plastic or metal materials.

FIG. 1 illustrates the outflow conduit 16 extending longitudinally from the outflow end 24 of the heart valve 20 and terminating in an end 46 distal the heart valve. At least one, and preferably a plurality of substantially flexible, resilient supports, such as flexible rings 50, are disposed about the elongated sidewall 52 of outflow conduit 16. The rings 50 are axially spaced apart intermediate the outflow end 24 of the heart valve 20 and the distal end 46 of the outflow conduit 16.

The rings 50 preferably are formed of a plastic-like material, such as Delrin, although other flexible and resilient materials including metal, may be used. The rings 50 should be formed of, or at least covered with a biocompatible material such as pericardial tissue described below. While the rings 50 are illustrated as right circular cylindrical rings, it will be appreciated that other shapes and configurations of flexible supports also may be used. For example, one or more substantially helical cylinders, suitably springs, or a flexible annular ring of a suitable mesh, may be mounted around the outflow conduit 16 to provide sufficient stiffness and resilience to resist compression.

Biocompatible material, such as an outer sheath 54 of pericardium, is attached to the apparatus 10 to cover each of the rings 50. Preferably, the sheath 54 is secured to the apparatus 10 by sutures 55 at the outflow end 24 and at end 46. In this embodiment, additional sutures 56, such as mattress sutures, are applied around each ring 50 and further secure the rings to the inner conduit portion 52 and to the outer sheath 54. The natural tissue outer sheath 54 reduces likelihood of the body rejecting the prosthesis, as the biological material has been fixed and detoxified in a suitable manner.

Individual sheets of a biological material also could be applied to cover each of the rings 50 and connected to the sidewall 52 of the longitudinally extending portion of the outflow conduit 16. This alternative approach is described below.

The inflow conduit 12 is attached to and extends longitudinally from the inflow end 22 of the heart valve 20. The inflow conduit 12 may be formed of a tubular sheath 60 of pericardial tissue or, alternatively, from a pulmonary artery (e.g. porcine or equine) similar to the outflow conduit 16. The sheath 60 preferably is extended to cover the stent element 32 that circumscribes the intermediate heart valve portion 14. Sutures 58, suitably mattress sutures, attach the stent element 32 to the sheath 60 and the underlying valve 20 at a desired axial position. Additional sutures 59 are used to secure the sheath 60 at the inflow end of the valve 20, with sutures 55 attaching the sheath adjacent outflow end 24.

Figure 2:
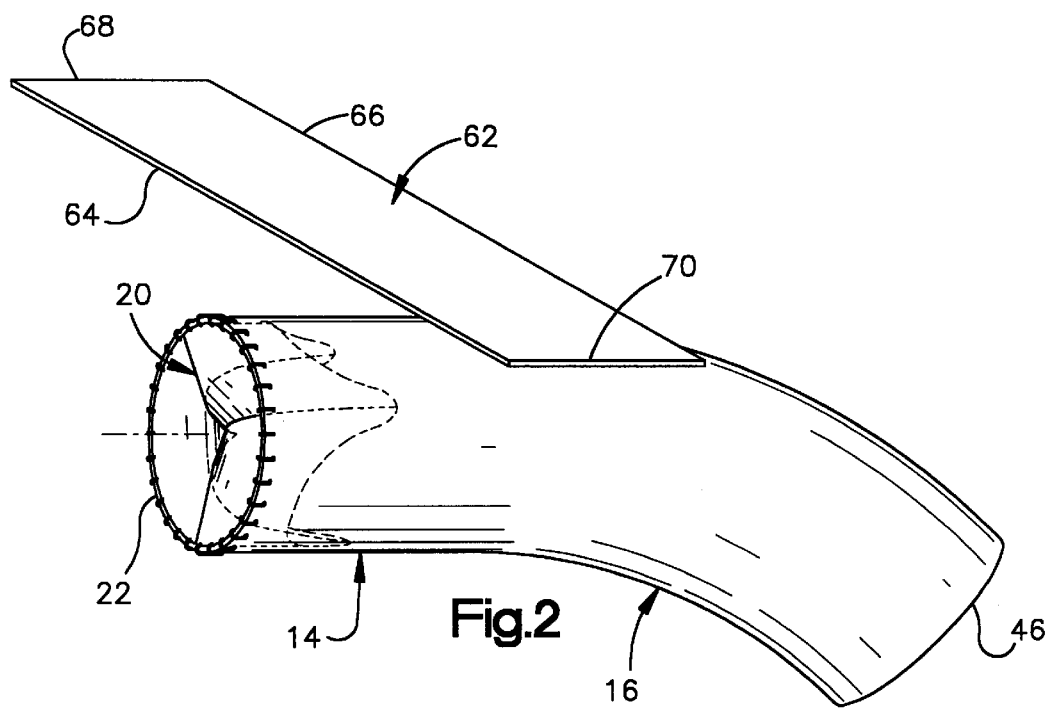

Preferred fabrication steps for the heart valve apparatus 10 are illustrated in FIGS. 2–4. In the preferred embodiment of FIG. 2, the intermediate heart valve conduit portion 14 and the outflow conduit 16 are integrally formed of the same pulmonary artery. In this preferred embodiment, the heart valve 20 also is formed of a pulmonic valve, preferably porcine or equine, that has been fixed in a suitable aldehyde solution with the pulmonary artery still attached and extending therefrom.

As stated above, however, the heart valve 20 also could be formed of a separate valve and subsequently attached to the outflow conduit 16 in a manner known in the art. The heart valve 20, for example, may be a natural tissue heart valve, a mechanical heart valve, or a hybrid valve formed of a combination of natural tissue and mechanical components mounted between the inflow and outflow conduits 12 and 16.

In the preferred embodiment of FIGS. 2 and 3, the intermediate conduit portion 14, which contains the heart valve 20, is covered with a sheet 62 of natural tissue, suitably equine or porcine pericardium. The sheet 62 forms a cylindrical sleeve mounted coaxially around the heart valve 20. Specifically, the sheet 62 has a first end 64 and a second end 66. The ends 64 and 66 are positioned at the respective inflow and outflow ends 22 and 24 of the heart valve 20. Preferably, ends 68 and 70 of the sheet 62 are wrapped circumferentially around the heart valve 20 and are secured to each other, end to end and with substantially no overlap. Accordingly, the length of the sheet 62 between ends 68 and 70 is substantially equal to the circumference of the heart valve 20. The ends 64 and 66 are sutured adjacent the respective inflow and outflow ends 22 and 24 of the heart valve, thereby defining the axial length of intermediate conduit portion 14.

After the sheet 62 has been secured to the heart valve 20, the stent element 32 and rings 50 are mounted to the apparatus 10 (see FIGS. 3 and 4). In particular, the flexible stent 32 is slid over the biological sheet 62 and around the heart valve 20 to a desired position between the inflow and outflow ends 22 and 24. The stent posts 34, 36, and 38 are appropriately aligned at the circumferential junctures of adjacent valve leaflets 26, 28 and 30. Once in position, the flexible stent 32 may be attached to the sheet by sutures 74. The sutures 74 need not provide a permanent attachment of the stent 32 to the heart valve 20, as subsequent sutures 58, shown in FIG. 1, perform this function.

Similarly, the rings 50 are positioned along the outflow conduit 16 in an axially spaced apart relationship between the edge 66 of the sheet 62 and the distal end 46 of the outflow conduit 16. Sutures 76 also may be used to attach the flexible rings 50 at the desired locations along the outflow conduit 16. Again, such sutures 76 need not be permanent, as the subsequent sutures 56 provide a more permanent attachment. The amount of structural support provided by the rings 50 is dependent upon several factors, including the number of rings, the axial length of such rings, as well as the radial thickness of the rings. Preferably, the sidewall of the rings 50 have a radial thickness of less than about 1 mm.

The final steps to complete the apparatus 10, in accordance with the embodiment of FIG. 1, is the application of the outer covering 54 and the attachment of the inflow conduit 12. The outer covering 54 may be in the form of a tubular piece of conduit that is slid over the outflow conduit 16 or, more preferably, in the form of a sheet of pericardial tissue similar to sheet 62 that is applied around the rings 50 and the outflow conduit 16. The sutures 76 maintain the position of the ring 50 as the outer covering 54 is applied. The outer covering 54 also may be sufficiently long as to cover both the intermediate and outflow conduit portions 14 and 16. The outer covering 54 also could be of sufficient length to form the inflow conduit 12, in addition to covering the rest of the apparatus 10.

Once the outer covering 54 is in position, appropriate sutures 56 and 58 are applied to secure the stent 32 and rings 50, respectively, along the apparatus 10. The sutures 56 and 58 provide a dual purpose. They maintain the axial position of the stent 32 and rings 50 as well as secure the outer covering 54 to the intermediate and outflow conduits 14 and 16, respectively.

As shown in FIG. 5, the apparatus 10 provides an extra-anatomic replacement valve for a tricuspid heart valve. Specifically, the heart valve apparatus 10 is mounted to the heart 80 to provide an external bypass of the tricuspid valve between the right atrium 82 and the right ventricle 84 of the heart. Either or both of the inflow conduit 12 or the outflow conduit 16 may be cut to make the heart valve apparatus 10 a proper length to fit between the right atrium 82 and right ventricle 84.

The distal end 46 of the outflow conduit is anastomosed by sutures 86 to the heart 80 over the right ventricle 84. Once the end 46 is secured loosely to the heart, for example, an aperture is formed through the heart 80 into the right ventricle 84. The sutures 86 are then tightened to provide a substantially liquid tight seal to the heart 80 around the aperture. The valve 20 inhibits the flow of blood from the right ventricle 84 which advantageously results in relatively little blood loss. Accordingly, there is no compelling need to place the patient on cardiopulmonary bypass when implanting the apparatus 10.

Similarly, end 45 of the inflow conduit 12 is anastomosed by sutures 88 to the heart over an aperture formed into the right atrium 82. The apertures into the right atrium 82 and right ventricle 84 may be formed by cutting or coring through the heart muscle. Once the apparatus 10 is in place, the tricuspid valve of the heart 80 is permanently closed, suitably by sutures, so that the flow of blood is, in turn, routed through the heart valve apparatus 10 rather than through the heart's own valve.

The heart valve 20 preferably is a pulmonic heart valve, suitably equine or porcine. The leaflets of a pulmonic heart valve advantageously provides for substantially free flow of blood through the apparatus 10 at the generally low pressure levels inherent in the right side of the heart 80. The rings 50 and stent 32 provide support against radial forces caused by pressure from a patient's sternum.

FIG. 6 illustrates an alternative embodiment of a heart valve apparatus 110 in accordance with the present invention. The heart valve apparatus 110 includes an inflow conduit portion 112, an intermediate conduit portion 114, and an elongated outflow conduit portion 116. The intermediate conduit portion 114 includes a heart valve 120 having an inflow end 122 and an outflow end 124, with a generally cylindrical valve wall portion 126 extending between the inflow and outflow ends of the valve 120. The intermediate conduit portion 114 defines a generally cylindrical tube 129 having a first substantially circular end 125 adjacent the inflow end 122 of the heart valve 120 and terminating in a substantially circular second end 127 adjacent the outflow end 124 of the valve.

The heart valve 120 includes a plurality of valve leaflets 128, 130 and 132 (see FIG. 8), which open and close about the heart valve axis A to permit the flow of blood from the inflow conduit 112 through the valve and to the outflow conduit 116. The valve leaflets 128, 130, and 132 also exhibit substantial coaptation, as to prevent the flow of blood from the outflow conduit 116 to the inflow conduit 112. The heart valve 120 preferably is a heart valve prosthesis, such as shown and disclosed in U.S. patent application Ser. No. 052,707, now U.S. Pat. No. 5,935,163, U.S. Pat. No. 5,861, 028, or U.S. Pat. No. 5,855,602, which are assigned to Shelhigh, Inc. and incorporated herein by reference.

It will be appreciated, however, that other configurations of heart valves, such as natural tissue heart valves, mechanical heart valves or combinations of natural tissue and mechanical heart valves, may be used in accordance with the present invention. Such valves could be covered with natural tissue to define conduit portion 114.

In the preferred embodiment, a substantially flexible stent element 134 is disposed circumferentially about the heart valve 120 intermediate the inflow and outflow ends 122 and 124, respectively. The flexible stent element 134 has an inflow end 136 and an outflow end 138 which are respectively spaced from the inflow and outflow ends 122 and 124 of the heart valve 120. Preferably, the inflow and outflow ends 136 and 138 of the stent 134 are contoured according to the respective inflow and outflow ends 122 and 124 of the heart valve 20. Alternatively, a simple annular ring, could be used to provide desired structural integrity to the heart valve. An annular ring without stent posts may be used, for example, when the individual outflow ends of the valve 120 have axially extending lobes or flanges that are secured to the interior of tube 129 or to outflow conduit 116, as disclosed in the above incorporated U.S. patent application.

The outflow conduit 116 extends longitudinally from the outflow end 124 of the heart valve 120. Preferably, the outflow conduit 116 has a first end 144 anastomosed by sutures to the outflow end 127 of conduit portion 114 and terminates in a spaced apart end portion 146. As with the embodiment of FIGS. 1–5, the outflow conduit 116 may be formed of a tubular artery or a sheet that is formed into a generally cylindrical tube. The first end 144 of the outflow conduit 116 is selected to have a diameter substantially equivalent to the diameter of the outflow end 127 of conduit portion 114.

A support or a plurality of supports 150 preferably are disposed about the outflow conduit 116 to provide desired support. While a plurality of substantially flexible and resilient rings 150 is preferred, other configurations of supports, such as C-shaped members, a generally cylindrical mesh, or one or more cylindrical helixes, also may be used with substantially equal facility. The supports inhibit radial compression and stenosis of the outflow conduit 116.

In the preferred embodiment of FIG. 6, a plurality of rings 150 are mounted to the outflow conduit 116 in an axially spaced apart relationship. The rings 150 may be formed of a plastic-like material, such as Delrin, or another substantially flexible, resilient material such as metal. Each of the rings 150 is covered with a layer of detoxified biological material 152, suitably equine or porcine pericardium, to provide improved biocompatibility.

In addition or as an alternative to the support 150, the outflow conduit 116 preferably includes a plurality of substantially circumferentially extending corrugations or crimps 154. The corrugations 154 are formed in the sidewall 156 of the outflow conduit 116 intermediate ends 144 and 146.

The corrugations 154 are formed in the cylindrical sidewall 156 of outflow conduit 116, such as by fixing a substantially fresh sheet or tube of natural tissue (e.g., pericardium) in a suitable aldehyde solution. In order to form the desired corrugations, for example, the natural tissue may be mounted over an appropriately shaped die or mandrel having the desired surface corrugations. The tissue may be in the form of a tube or a sheet during the fixation process. The resulting corrugations 154 in sidewall 156 facilitate bending and flexing of the outflow conduit 116 while resisting fracture thereof. Thus, the corrugations 154 need only be formed along the part of sidewall portion 156 which may be subjected to bending. The corrugations 154 also increase the structural rigidity of the conduit 116 to inhibit stenosis of the conduit.

An implantation member 160 is attached at the end 146 of the outflow conduit 116 to facilitate implantation of the apparatus 110. The implantation member 160 is formed of a generally rigid and tubular portion 162 configured for insertion into the left ventricle through the apex of the heart. Accordingly, the tubular portion must be of sufficient length to penetrate completely through the thick tissue at the apex. The tubular portion 162 has about the same diameter as the conduit 116 at end 146. The implantation member 160 also includes an annular implantation flange 164 that is attached to and extends radially outwardly from the tubular portion 162 adjacent the end 146 of the outflow conduit 116. The implantation flange 164 may be formed of natural tissue, such as equine or porcine pericardium, or from an appropriate textile material, such as dacron. Where a textile or other synthetic material is used to form flange 164, the flange preferably is covered with a natural tissue (e.g., pericardium) to improve biocompatibility.

The inflow conduit 112, which is formed of an elongated flexible material, extends longitudinally from the inflow end 125 of conduit portion 114. The inflow conduit 112 includes a first end 168 having a diameter approximating the diameter of conduit portion 114 and a second end 170 spaced apart from the first end 168. The first end 168 is anastomosed to end 125 of the intermediate conduit portion 114 by sutures in a known manner.

Similar to the outflow conduit 116, the inflow conduit 112 also may include a sidewall portion 171 having a plurality of axially spaced apart corrugations 172 to facilitate flexing or bending of the inflow conduit 112. A support, such as plurality of flexible rings 173 also may be mounted to the exterior of the inflow conduit 112 between the ends 168 and 170 to further enhance its structural integrity.

Figure 9:
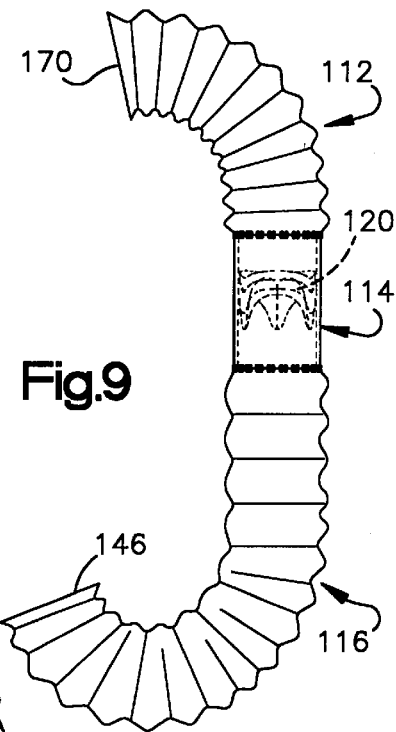
FIG. 9 illustrates an intermediate fabrication step for the heart valve apparatus of FIG. 6.

The construction of the embodiment of the heart valve apparatus 110 shown in FIG. 6 may be better appreciated with reference to FIGS. 7–9. Preferably, the heart valve 120 is formed of a stented or semi-stented heart valve prosthesis, such as disclosed in the above-incorporated references. The prosthesis 120 includes the flexible stent element 134 or other appropriate structural support element, such as an annular ring, to provide additional resilient support and resist stenosis.

A sheet 174 of biocompatible material, such as equine or porcine pericardium, is mounted over the stent 134 and heart valve 120 to define the tubular sidewall portion 129 of conduit portion 114. This is substantially similar to sheet 62 described with respect to FIGS. 1–5. The sheet 174 preferably is attached coaxially around the heart valve 120 with substantially no overlap at abutting ends 176 and 178. Also, spaced apart side edges 180 and 182 define the respective inflow and outflow ends 125 and 127 of conduit portion 114. As shown in FIG. 8, the inflow and outflow conduits 112 and 116 are anastomosed to the respective inflow and outflow ends 125 and 127 of conduit portion 114 in a known manner. This structure, without rings 150 and 173 and implantation member 160, is illustrated in FIG. 9. It will be appreciated that the apparatus shown in FIG. 9 may be used to provide an extra-anatomical bypass for a defective heart valve, either mitral or tricuspid.

The outflow and inflow rings 150 and 172 may be secured, suitably by sutures, about the corrugated inflow and outflow conduits 112 and 116 before or after attaching the conduit portions together. Similarly, the implantation member 160 may be attached to the distal end of the outflow conduit 116 before or after its attachment at the outflow end 124.

An outer covering 188 and 190 of a biocompatible material, such as equine or porcine pericardium, covers the inflow and outflow rings 173 and 150, respectively. Preferably, the outer covering is formed of individual sheets 188 and 190 mounted over each of the respective rings 150 and 173. As shown in the exploded view of FIG. 7, the outer covering 190 preferably covers the entire ring 150. The outer coverings 188 and 190 preferably is formed of a sheet of pericardium mounted over each ring 150 by appropriate sutures prior to mounting onto associated conduits 112 and 116. The outer coverings 188 and 190 also could be mounted about the exterior of the rings 150 and 173 after being positioned about the associated conduit portions.

In this embodiment, the outer coverings 188 and 190 are secured to the respective outflow and inflow conduits 112 and 116, such as by sutures 189 and 191, positioned around each of the rings 150 and 173, thereby connecting the outer coverings 188 and 190 to the respective conduit portions 112 and 116. The sutures maintain the rings 150 and 172 at a desired axial position along associated conduit portions as well as secure the biocompatible outer covering to the conduits.

It will be appreciated that biocompatible sheets of greater axial length, suitably corrugated, also may be used to cover adjacent outflow rings 150 and inflow rings 173. A similar arrangement of sutures may be used to attach such other configurations of outer coverings with the associated inflow and outflow conduits 112 and 116.

Figure 10:
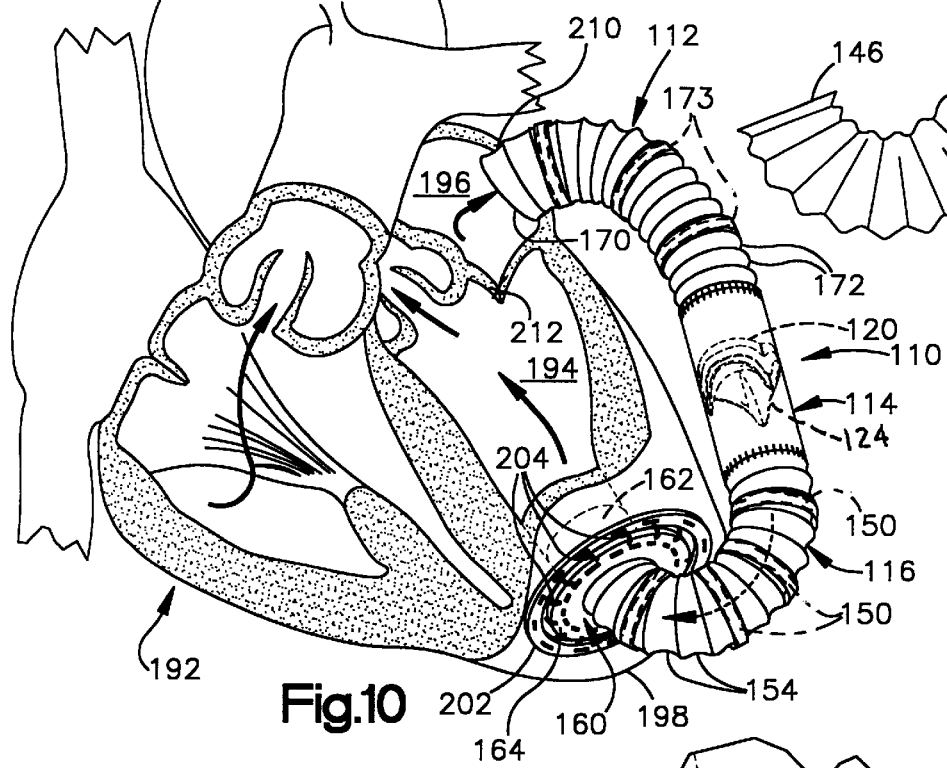
FIG. 10 illustrates the heart valve apparatus of FIG. 6 mounted to a heart in accordance with a preferred embodiment of the present invention.

FIG. 10 illustrates the heart valve apparatus 110 anastomosed to a heart 192 in accordance with a preferred embodiment of the present invention. Specifically, the implantation member 160 of the outflow conduit 116 is fluidly connected with the left ventricle 194 and the inflow conduit 112 is fluidly connected to the left atrium 196.

In the preferred embodiment of FIG. 10, the tubular portion 162 of the implantation member 160 is inserted into an aperture formed in the apex 198 of the heart 192. A suitable aperture is formed through the apex 198 into the left ventricle 194, for example, by cutting or coring through the heart 192 in a known manner. Some blood from the left ventricle 194 may enter the outflow conduit 116 but will be blocked upon engaging the leaflets at the outflow end 124 of the heart valve 120. This typically results in relatively little blood loss and, in turn, no compelling need to place the patient on cardiopulmonary bypass during the operation.

The implantation flange 164 provides an annulus to suture the outflow conduit 116 to the apex 198 of the heart 192. In order to provide a more secure connection at the apex 198, an annular ring 202 is positioned against the apex in a circumscribing relationship with the implantation flange 164. The annular ring 202 has an inner diameter which is greater than the outer diameter of the implantation flange 164 and is connected with the implantation flange through appropriate sutures 204. Preferably, the annular ring 202 is formed of a biological material, such as pericardium, which has been fixed in an appropriate aldehyde solution. Alternatively, other biocompatible materials may be used to form the annular ring 202.

Figure 11:
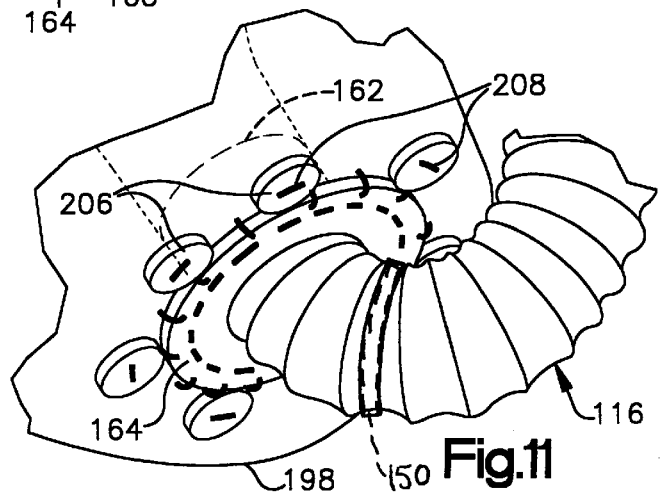
FIG. 11 illustrates an alternative approach for attaching the apparatus of FIG. 6 to a heart.

FIG. 11 illustrates an alternative approach for securing the outflow conduit 116 to the apex 198 of the heart 192. A plurality of substantially circular pledgets 206, preferably formed of a biological tissue (e.g. pericardium), are attached to the heart 192 in a spaced apart relationship circumscribing the implantation flange 164. Additional sutures 208 connect the implantation flange 164 with the apex 198 and the surrounding pledgets 206. The circular pledgets 206, like the annular ring 202, further reinforce the attachment of the apparatus 110 at the apex 198 of the heart 192.

The corrugations 154 and 172 along the inflow and outflow conduits 112 and 116 advantageously permit substantial bending. This enables the apparatus 110 to be manipulated so that the opposite end 170 can be easily positioned and attached at the left atrium 198. The end 170 of the inflow conduit 112 is anastomosed to the left atrium by sutures 210. The sutures 210 may be kept loose at first so that, once in place, an appropriately sized aperture may be cut into the left atrium beneath end 170. After the aperture is formed the tricuspid valve 212 may be permanently closed, such as by sutures. The sutures 210 are then tightened to anastomose the inflow conduit 112 with the left atrium. Accordingly, blood will bypass valve 212 and flow through the apparatus 110.

It will be appreciated that all of the embodiments of the heart valve apparatus in accordance with the present invention may be implanted without placing the patient on cardiopulmonary bypass. This is because, unlike conventional heart valve prostheses, the apparatuses 10 and 110 in accordance with the present invention are not intended do not physically replace the defective heart valve inside the heart. Instead, the apparatuses 10 and 110 each provide an externally mounted, i.e., extra-anatomical, structure to reroute the flow of blood as to bypass the defective valve.

It further will be appreciated that the corrugated conduits 112 and/or 116 described with respect to FIGS. 6–10 also may be used in connection with the mitral valve replacement shown and described relative to FIGS. 1–5. One also might select other desirable features from the various embodiments described herein to form an extra-anatomic valve apparatus for replacing a mitral or tricuspid valve.

One skilled in the art of heart valve prosthetics further will understand and appreciate that other configurations of ring supports 50, 150 also may be used. For example, a cylindrical helix or mesh may be mounted about conduit portions to provide desired resilient support of conduit portions 12, 112 and 16, 116. Similarly, corrugations 154, 172 may be in the form of axially wound helical ribs formed in the sidewall portion of the associated conduits.

From the above description of the invention, those skilled in the art will perceive improvements, changes and modifications. Such improvements, changes and modifications within the skill of the art are intended to be covered by the appended claims.

Having described the invention, the following is claimed:

1. An extra-anatomic heart valve apparatus comprising:
   a heart valve having an inflow end, an outflow end and a central axis extending through the inflow and outflow ends;
   a substantially flexible stent element disposed substantially coaxially about said heart valve intermediate the inflow and outflow ends of said heart valve;
   an elongated outflow conduit extending longitudinally from the outflow end of said heart valve and terminating in a distal end spaced from said heart valve;
   at least one resilient support disposed about said outflow conduit intermediate the outflow end of said heart valve and the distal end of said outflow conduit; and
   an outer sheath of biological material connected with said outflow conduit and covering said a least one resilient support.

2. An apparatus as set forth in claim 1 wherein said outflow conduit has a sidewall formed of biological material.

3. An apparatus as set forth in claim 1 further comprising a sheath of biological material mounted coaxially around said heart valve and said flexible stent element to define a substantially cylindrical sidewall portion around said heart valve, said sheath having a first end portion connected at the inflow end of said heart valve and a second end portion spaced axially from the first end portion adjacent the outflow end of said heart valve, the second end portion of said sheath being connected with said outflow conduit.

4. An apparatus as set forth in claim 3 wherein said heart valve is formed of a pulmonic heart valve.

5. An apparatus as set forth in claim 4 wherein at least part of said outflow conduit is formed of a pulmonary artery which also forms the outer sidewall portion of said pulmonic heart valve.

6. An apparatus as set forth in claim 5 wherein said resilient support includes a plurality of rings connected about said pulmonary artery in an axially spaced apart relationship.

7. An apparatus as set forth in claim 1 wherein said outflow conduit further includes a plurality of circumferentially extending corrugations intermediate the outflow end of said heart valve and the distal end of said outflow conduit.

8. An apparatus as set forth in claim 7 wherein said outflow conduit has a generally cylindrical sidewall formed of a biological material, said corrugations being formed in the cylindrical sidewall of said outflow conduit.

9. An apparatus as set forth in claim 7 further including a generally rigid, tubular implantation member extending longitudinally from the distal end of said outflow conduit, said implantation member having a sidewall portion which terminates in a first end spaced from the distal end of said outflow conduit, said implantation members also having an implantation flange extending outwardly from the sidewall portion of said implantation member spaced from the first end of said implantation member.

10. An apparatus as set forth in claim 9 further including a substantially planar annular ring having an inner diameter which is greater than an outer diameter of said implantation flange, said annular ring being connectable with and circumscribing said implantation flange through sutures.

11. An apparatus as set forth in claim 1 further including an elongated inflow conduit extending longitudinally from the inflow end of said heart valve, said inflow conduit having a first end connected adjacent the inflow end of said heart valve and terminating in a second end spaced from the inflow end of said heart valve.

12. An apparatus as set forth in claim 11 wherein said inflow conduit further includes a cylindrical sidewall having a plurality of circumferentially extending corrugations formed in the sidewall of said inflow conduit.

13. An apparatus as set forth in claim 12 further including at least one resilient support disposed circumferentially about said inflow conduit between the inflow end of said heart valve and the second end of said inflow conduit.

14. An apparatus as set forth in claim 13 wherein said at least one resilient support further includes a plurality of substantially flexible annular rings disposed circumferentially about said outflow conduit between the outflow end of said heart valve and the distal end of said outflow conduit, said plurality of annular rings being in an axially spaced apart relationship.

15. An apparatus as set forth in claim 14 further including biological material mounted to said outflow conduit to cover each of said plurality of flexible rings.

16. An extra-anatomic heart valve apparatus comprising:
   a first conduit portion having a substantially cylindrical sidewall with first and second spaced apart ends;
   a heart valve having inflow and outflow ends mounted within said first conduit portion between the respective first and second ends of said first conduit portion;
   an elongated second conduit portion extending longitudinally from the second end of said first conduit portion, said second conduit portion having a substantially cylindrical sidewall with a first end connected at the second end of said first conduit portion and terminating in a second end spaced apart from the first end of said second conduit portion; and
   a plurality of circumferentially extending corrugations formed in the sidewall of said second conduit portion.

17. An apparatus as set forth in claim 16 further including at least one resilient support circumferentially disposed about said second conduit portion and a biological material connected with said second conduit portion covering said at least one resilient support.

18. An apparatus as set forth in claim 17 wherein said at least one resilient support further includes a plurality of substantially flexible rings disposed about said second conduit portion, each of said rings being in an axially spaced apart relationship along said second conduit portion between the first and second ends of the second conduit portion.

19. An apparatus as set forth in claim 16 further including a third conduit portion extending longitudinally from the inflow end of said first conduit portion.

20. An apparatus as set forth in claim 19 wherein said third conduit further includes a substantially flexible elongated sidewall having a plurality of circumferentially extending corrugations formed in the sidewall of said third conduit.

21. An apparatus as set forth in claim 16 further including a generally rigid and tubular implantation member connected to and extending from the second end of said second conduit portion, said implantation member having a cylindrical outer sidewall and an implantation flange extending outwardly from the outer sidewall of said implantation member adjacent the second end of said second conduit portion.

22. An apparatus as set forth in claim 18 wherein said implantation flange of said implantation member has an outer diameter and said apparatus further includes an annular pledget having a central bore with an inner diameter that is greater than the outer diameter of said implantation flange, said annular pledget being connectable to and circumscribing said implantation flange through sutures.

23. An apparatus as set forth in claim 16 wherein said flexible stent element has inflow and outflow ends contoured according to the contour of the inflow and outflow ends of said heart valve, the inflow and outflow ends of said flexible stent element being spaced axially from the inflow and outflow ends of said heart valve.

24. An extra-anatomic heart valve apparatus comprising:
- a first conduit portion having a cylindrical sidewall with first and second ends;
- a heart valve having inflow and outflow ends mounted within said first conduit portion between the first and second ends of said first conduit portion;
- an elongated second conduit portion extending longitudinally from said first conduit portion, said second conduit portion having a cylindrical sidewall portion with a first end connected at the second end of said first conduit portion and terminating in a second end spaced apart from the first end of said second conduit;
- at least one resilient support circumferentially disposed about said second conduit portion; and
- a biological material connected with said second conduit portion covering said at least one resilient support.

25. An apparatus as set forth in claim 24 wherein said at least one resilient support further comprises a plurality of substantially flexible rings disposed about said second conduit portion, said rings being in an axially spaced apart relationship along said outflow conduit; and
- biological material connected with said second conduit portion covering each of said plurality of rings of said second conduit portion.

26. An apparatus as set forth in claim 24 wherein said second conduit portion further includes a cylindrical sidewall formed of biological material having circumferentially extending corrugations formed in the cylindrical sidewall of said second conduit portion intermediate the outflow end of said heart valve and the second end of said second conduit portion.

27. An apparatus as set forth in claim 24 further including an elongated inflow conduit connected to and extending longitudinally from the first end of said first conduit portion, said inflow conduit having a first end adjacent said inflow end of said heart valve and a second end spaced from the inflow end of said heart valve.

28. An extra-anatomic heart valve apparatus comprising:
- a heart valve having an inflow end, an outflow end and a central axis extending through the inflow and outflow ends;
- a substantially flexible stent element disposed about said heart valve intermediate the inflow and outflow ends of said heart valve;
- a generally cylindrical sheath of biological material being mounted coaxially about said valve and said stent element, said sheath having an axial length about equal to or greater than the axial length of said heart valve, said sheath having a first end adjacent said inflow end of said heart valve and a second end adjacent said outflow end of said heart valve;
- an elongated, flexible outflow conduit having a sidewall connected to and extending longitudinally from the second end of said sheath and terminating in a distal end spaced from said heart valve, a plurality of circumferentially extending corrugations formed in the sidewall of said outflow conduit;
- a generally rigid, tubular implantation member connected to and extending from the distal end of said outflow conduit, said implantation member having an outer sidewall with an implantation flange extending outwardly from the outer sidewall of said implantation member adjacent the second end of said second conduit portion; and
- an elongated, flexible inflow conduit connected to and extending longitudinally from the first end of said sheath.

29. An apparatus as set forth in claim 28 further comprising a plurality of resilient support members attached about said outflow conduit in an axially spaced apart relationship, each of said support members being covered with a biological material.

* * * * *